United States Patent [19]

Garabedian

[11] Patent Number: Plant 5,291

[45] Date of Patent: Oct. 9, 1984

[54] PLUM TREE, LATE SALVADOR

[76] Inventor: John M. Garabedian, 3104 Huntington Blvd., Fresno, Calif. 93702

[21] Appl. No.: 463,895

[22] Filed: Feb. 4, 1983

[51] Int. Cl. ..... A01H 5/00

[52] U.S. Cl. ..... Plt./38

[58] Field of Search ..... Plts./30

*Primary Examiner*—James R. Feyrer

*Attorney, Agent, or Firm*—Huebner & Worrel

[57] ABSTRACT

A plum tree generally similar to the Roysum plum tree (U.S. Plant Pat. No. 2,619) which it most nearly resembles and approximately with which it ripens, bearing symmetrical, medium-sized fruit having dark red to dark purplish-red skin, yellowish-amber, semi-freestone flesh, and of superior flavor.

1 Drawing Figure

BACKGROUND OF THE NEW VARIETY

The present invention relates to a new and distinct variety of plum tree broadly characterized by its regular and productive bearing of dark red to dark purplish-red fruit which has a heavy, blue-gray bloom, and ripens late in the season, approximately with the Roysum plum (U.S. Plant Pat. No. 2,619).

The Roysum plum tree is well known as being a regular bearer of medium sized, freestone fruit having a skin of red to blue hue, and having good shipping and keeping qualities. The desirability of the Roysum plum is further enhanced by the relative absence of competition from other plums due to the late ripening of its fruit.

Important among those factors contributing to the commercial success of fruit varieties, and in particular plums, are the appearance of the fruit and the period in the season when the fruit can be marketed. An attractive, symmetrical plum obviously more readily gains market acceptance than a plum not exhibiting these desirable characteristics. Such a plum commands a relatively greater share of the market if it can be harvested late enough in the season to avoid direct competition with other, better known plums having generally similar appearances. Therefore, it has long been recognized as desirable to provide a plum tree which bears fruit having dark red to purplish-red skin, a symmetrical shape and satisfactory size, and which ripens late in the season, remaining firm and ripe on the tree for a substantial period in order that its fruit may be harvested at an optimum time.

ORIGIN AND ASEXUAL REPRODUCTION OF THE NEW VARIETY

My new variety of plum tree was discovered by me in 1968 growing as a seedling of a Salvador plum tree (unpatented). The orchard was, at the time of discovery, and is owned by me and is located at Church and Greenwood Avenues near the City of Sanger, in the County of Fresno, in the State of California.

I asexually reproduced the new variety in 1971 by budding it onto seedling rootstock in an orchard on a ranch owned by me at Kings Canyon Road and Fowler Avenue near the City of Fresno, in the County of Fresno, in the State of California. Fruit and tree characteristics of plum trees resulting from such budding were found to be identical to those of the original seedling.

SUMMARY OF THE NEW VARIETY

The instant variety of plum tree is generally characterized by bearing fruit having a dark red to dark purplish-red skin and yellowish-amber flesh and which ripens approximately on October 15, or roughly at the same point in the season as the Roysum plum. The Late Salvador of my new variety exhibits a number of superior characteristics in comparison with the Roysum plum, among which are its darker skin color, its heavier, blue-gray bloom, and relatively mild, good eating flavor. The fruit of the instant variety further distinguishes itself from the Roysum plum in its uniform, symmetrical, broad oval to globose form and by its skin which demonstrates no detected tendency to crack.

The fruit of the new variety is semi-freestone of medium size, and has evenly ripening flesh with a slightly subacid flavor. An important feature of the new variety is the ability of its fruit to remain on the tree for a substantial period of time after ripening without a deterioration in its condition. In 1982, the fruit was hard ripe on October 15 and remained so on the tree until mid-November. Thus, in addition to its late season of maturity, the Late Salvador is further possessed of the desirable characteristic of being able to be harvested during a broad time period, allowing the commercial grower great latitude in selecting the date on which it is most advantageous to pick the plums for market.

BRIEF DESCRIPTION OF THE DRAWING

The accompanying drawing is a color photograph of a representative twig bearing three plums with the bloom characteristic of the new variety; a plum divided to show the flesh color and the pit cavity; three plums showing, respectively, the suture aspect, the apical aspect, and the cheek aspect; and a representative twig showing characteristic leaves.

DETAILED DESCRIPTION

Referring more specifically to the pomological details of this new and distinct variety of plum tree, the following characteristics have been observed under the ecological conditions prevailing at the designated orchard in Fresno County, Calif. All of the color code plate indications are by reference to the Maerz and Paul *Dictionary of Color,* except where common terms of color definition are employed.

TREE

Size: Medium, medium vigor.
Figure: Upright, medium density, vase formed.
Productivity: Productive, regular bearer.
Trunk: Thickness — medium.
*Texture.*—Medium.
*Color.*—Bark Plt 16-A-6 (Taupe).
*Striations.*—Plt 11-D-6 to Plt 16-A-12 (Bishra Date).
Branches:
*Thickness.*—Medium.
*Texture.*—Medium to shaggy (rough, small exfoliated plates adhering).
*Lenticels.*—Numerous to medium, medium size, inconspicuous.
*Color.*—Same as trunk.
Leaves:
*Shoot.*—Size — Medium, length, 9.48±1.00 cm.; width, 4.23±0.62 cm. Shape — ovate, medium thickness, acutely pointed. Texture — nearly smooth. Color — upper surface, Plt 25-L-8. Lower surface, Plt 21-D-5. Margin — crenate. Petiole — medium length, 1.09±0.19 cm.; medium thickness. Glands — 0 to 2 small, green, globose glands at opposite sides of base of blades. Stipules — linear, small, deciduous.
*Spur.*—Size — length 10.0±0.92 cm.; width 3.46±0.38 cm. Shape — obovate; apex — acuminate; base — acute, medium. Color — medium green. Texture — nearly smooth. Margin — crenate. Petiole — medium length and thickness compared to shoot leaf petioles, 1.56±0.23 cm. long. Glands — usually none, occasionally one, rarely two small, green, globose glands at base of blade, lacking stipules.
Buds: Small; short; pointed; free; glabrous.
Flowers:
*Dates of bloom.*—In 1982, first bloom on February 20 and full bloom on March 2; early to medium compared with other varieties.
*Size.*—Medium.
*Color.*—White.

FRUIT

Maturity: Hard ripe approximately October 15, remaining hard ripe on tree until mid-November.
Size: Uniformly medium; axial diameter — 5.73±0.20 cm.; transverse diameter in suture plane — 5.83±0.28 cm.; diameter in cheek plane — 5.97±0.28 cm.
Form: Uniform; symmetrical; broad oval to globose.
*Cheek.*—Broadly oval to globose.
*Suture.*—Broadly oval to oval; truncated at base and usually at apex.
*Axial aspect.*—Round or nearly round.
Suture: Varying from an inconspicuous line to a shallow groove extending from base to apex.
Ventral surface: Rounded very slightly; lipped throughout; lips equal.
Stem cavity: Abrupt, slightly elongated in suture plane with suture showing on one side; depth — 0.71±0.15 cm.; breadth — 1.81±0.10 cm.; unmarked.
Base: Rounded to truncate.
Apex: Short, truncate; slightly depressed.
Pistil point: Apical.
Skin: Medium thickness and toughness; tenacious to flesh; no tendency to crack.
*Color.*—Full colored; dark red, Plt 56-L-11 to dark purplish-red, Plt 48-L-11.
*Bloom.*—Heavy, medium bluish gray, Plt 37-B-6.
*Dots.*—Small, light brown; few, scattered, usually more numerous apically.
Flesh:
*Color.*—Yellowish-amber, Plt 10-H-5.
*Amygdalin.*—Wanting.
*Juice.*—Scant.
*Texture.*—Firm, crisp, meaty.
*Fibers.*—Few, fine, tender.
*Ripening.*—Even.
*Flavor.*—Slightly subacid; mild.
*Aroma.*—Wanting.
*Eating quality.*—Good.
Stone: Semi-free; adheres to flesh along both dorsal and ventral edges; short fibers.
*Size.*—Length — 2.16±0.16 cm.; breadth — 1.73±0.12 cm.; thickness — 0.90±0.07 cm.
*Form.*—Broad oval; base straight, often necked; hilum narrow, oblong.
*Cheek aspect.*—Broad, oval, occasionally nearly round; base often eroded ventrally; occasionally necked.
*Suture aspect.*—Narrow ovate.
*Axial aspect.*—Narrow oval, with ventral suture protruding.
*Apex.*—Rounded, sometimes with a short, blunt tip.
*Sides.*—Equal.
*Surface.*—Very lightly and irregularly ridged near base; roughened, often very finely pitted (eroded) medially.
*Ventral edge.*—Thin, without wings; suture line thickened, interrupted with deep grooves laterally from base to near apex.
*Dorsal edge.*—Narrow; usually with deep groove from near base to near apex; sides sharp, somewhat eroded.
*Color.*—Light brown; somewhat mottled; basic color approximates Plt 10-D-8.
Use: Market, dessert, culinary.
Keeping quality: Good.
Shipping quality: Good.
Resistance to insects: Medium.
Resistance to diseases: Medium.

Although the new variety of plum tree possesses the described characteristics as a result of the growing conditions in Fresno County, Calif., in the central portion of the San Joaquin Valley, it is to be understood that variations of the magnitude and characteristics incident to growing conditions, fertilization, pruning, pest control, and other horticultural practices are to be expected.

Having thus described and illustrated my new variety of plum tree, what is claimed as new and desired to be secured by Letters Patent is:

1. A new and distinct variety of plum tree substantially as illustrated and described and broadly characterized by the late season of its fruit's maturity, approximately with that of Roysum (U.S. Plant Pat. No. 2,619), but differing from Roysum in its regular and productive bearing of dark red to dark purplish-red fruit having a heavier, blue-gray bloom and relatively mild good flavor.

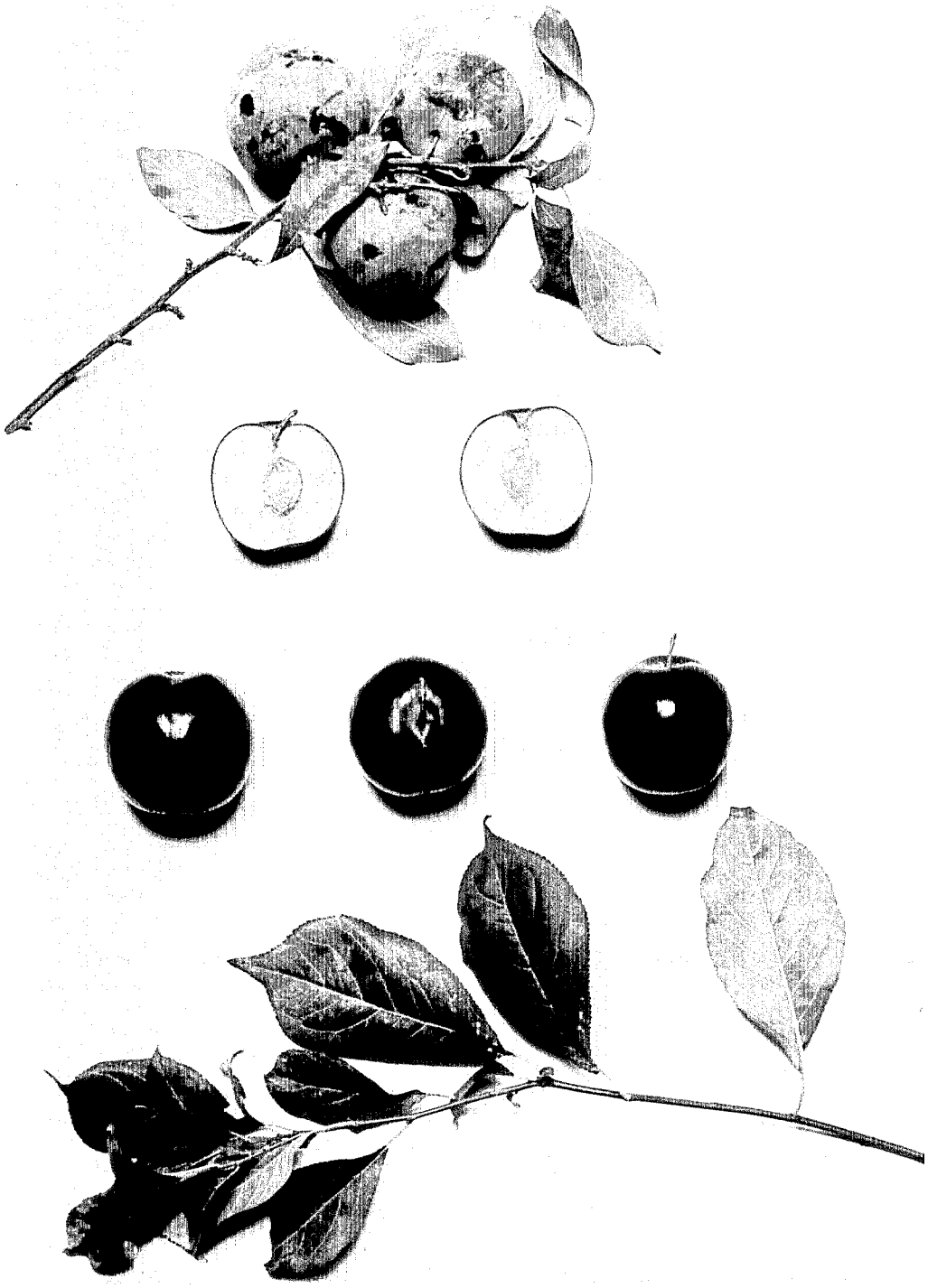

* * * * *